(12) United States Patent
Munoz

(10) Patent No.: US 12,232,708 B2
(45) Date of Patent: Feb. 25, 2025

(54) VAGINAL SPECULUM AND RELATED METHODS

(71) Applicant: Andrea Munoz, Encinitas, CA (US)

(72) Inventor: Andrea Munoz, Encinitas, CA (US)

( * ) Notice: Subject to any disclaimer, the term of this patent is extended or adjusted under 35 U.S.C. 154(b) by 67 days.

(21) Appl. No.: 17/226,802

(22) Filed: Apr. 9, 2021

(65) Prior Publication Data

US 2021/0369100 A1    Dec. 2, 2021

Related U.S. Application Data

(60) Provisional application No. 62/972,952, filed on Feb. 11, 2020.

(51) Int. Cl.
| | |
|---|---|
| *A61B 1/303* | (2006.01) |
| *A61B 1/00* | (2006.01) |
| *A61B 1/07* | (2006.01) |
| *A61B 1/32* | (2006.01) |
| *A61M 29/00* | (2006.01) |
| *A61B 17/02* | (2006.01) |

(52) U.S. Cl.
CPC .......... *A61B 1/303* (2013.01); *A61B 1/00066* (2013.01); *A61B 1/07* (2013.01); *A61B 1/32* (2013.01); *A61M 29/00* (2013.01); *A61B 17/0293* (2013.01)

(58) Field of Classification Search
CPC .............. A61B 17/42; A61B 2017/345; A61B 2017/0225; A61B 1/32; A61B 1/303; A61B 5/4337; A61B 46/13
See application file for complete search history.

(56) References Cited

U.S. PATENT DOCUMENTS

| | | | | |
|---|---|---|---|---|
| 196,600 | A * | 10/1877 | Shiland | A61B 17/0218 600/201 |
| 4,046,140 | A * | 9/1977 | Born | A61B 1/04 600/184 |
| 4,432,351 | A * | 2/1984 | Hoary | A61B 1/32 600/220 |
| 5,605,161 | A * | 2/1997 | Cross | A61B 10/007 600/580 |
| 5,795,289 | A * | 8/1998 | Wyttenbach | A61B 1/32 606/198 |
| 6,004,265 | A * | 12/1999 | Hsu | A61B 1/32 600/223 |
| 6,036,638 | A * | 3/2000 | Nwawka | A61B 1/00142 600/220 |
| 6,402,700 | B1 * | 6/2002 | Richards | A61B 17/3431 600/562 |
| 6,527,710 | B1 * | 3/2003 | Davidson | A61B 1/32 600/222 |
| 6,902,530 | B1 * | 6/2005 | Pianka | A61B 1/00142 600/220 |
| 6,926,677 | B2 * | 8/2005 | Richards | A61B 17/3431 600/562 |

(Continued)

FOREIGN PATENT DOCUMENTS

| | | | | |
|---|---|---|---|---|
| EP | | 3260039 A1 * | 12/2017 | ......... A61B 1/00032 |
| WO | WO-9307800 A1 * | | 4/1993 | ............... A61B 1/32 |

*Primary Examiner* — Julianna N Harvey
*Assistant Examiner* — Anna V. Little
(74) *Attorney, Agent, or Firm* — Pierson Ferdinand LLP; Keats Quinalty

(57) ABSTRACT

Disclosed is speculum and related methods to comfortably dilate a woman's vaginal canal during a pelvic exam.

6 Claims, 8 Drawing Sheets

(56) References Cited

U.S. PATENT DOCUMENTS

| | | | | |
|---|---|---|---|---|
| 8,864,660 B1* | 10/2014 | Yufa | ............... | A61B 17/02 |
| | | | | 600/219 |
| 9,687,604 B2* | 6/2017 | Haueter | ............ | A61M 5/31525 |
| 2004/0225196 A1* | 11/2004 | Ruane | ............... | A61B 17/0206 |
| | | | | 600/220 |
| 2006/0256575 A1* | 11/2006 | Vayser | ............... | A61B 1/0011 |
| | | | | 362/804 |
| 2008/0058604 A1* | 3/2008 | Sorensen | ............... | A61B 1/32 |
| | | | | 600/208 |
| 2008/0146886 A1* | 6/2008 | Lucas | ............... | A61B 1/303 |
| | | | | 600/220 |
| 2009/0187081 A1* | 7/2009 | Kelly | ............... | A61B 1/32 |
| | | | | 600/235 |
| 2011/0301424 A1* | 12/2011 | Steigerwald | ............ | A61B 1/303 |
| | | | | 600/235 |
| 2013/0060095 A1* | 3/2013 | Bouquet | ............... | A61B 1/303 |
| | | | | 600/208 |
| 2015/0112148 A1* | 4/2015 | Bouquet | ............... | A61B 1/32 |
| | | | | 600/214 |
| 2016/0051663 A1* | 2/2016 | Kapil | ............... | A61K 31/522 |
| | | | | 435/5 |
| 2017/0181607 A1* | 6/2017 | Lalli | ............... | A61B 1/00154 |
| 2017/0281149 A1* | 10/2017 | Rolfes | ............... | A61B 1/303 |
| 2018/0235444 A1* | 8/2018 | Tsai | ............... | A61B 1/303 |
| 2018/0263480 A1* | 9/2018 | Lalli | ............... | A61B 1/0684 |
| 2019/0000486 A1* | 1/2019 | Prior | ............... | A61L 31/14 |
| 2019/0082948 A1* | 3/2019 | Ford | ............... | A61B 1/303 |

* cited by examiner

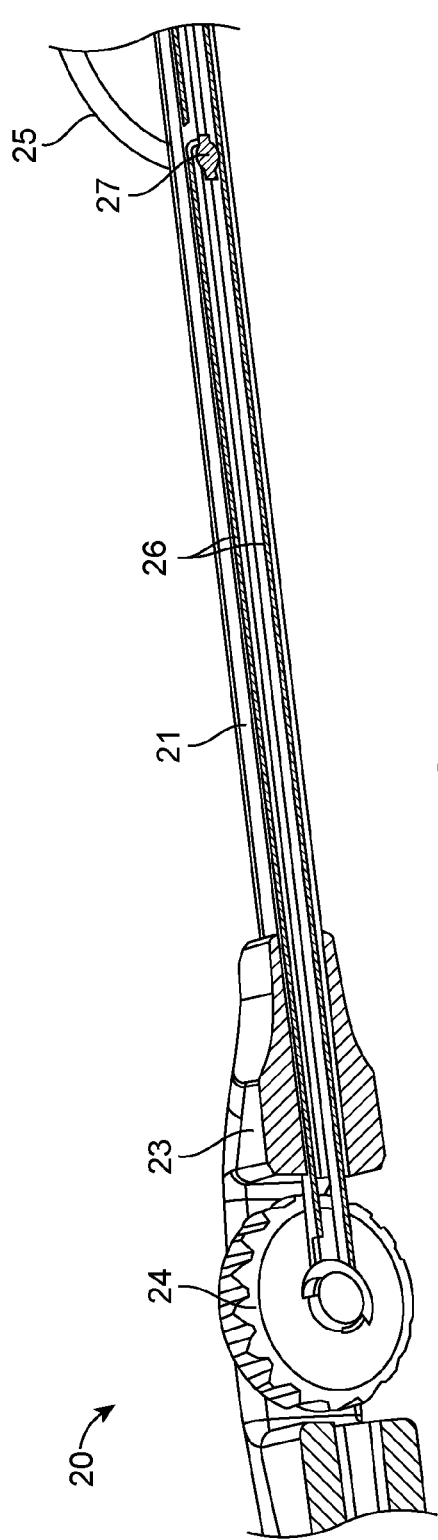
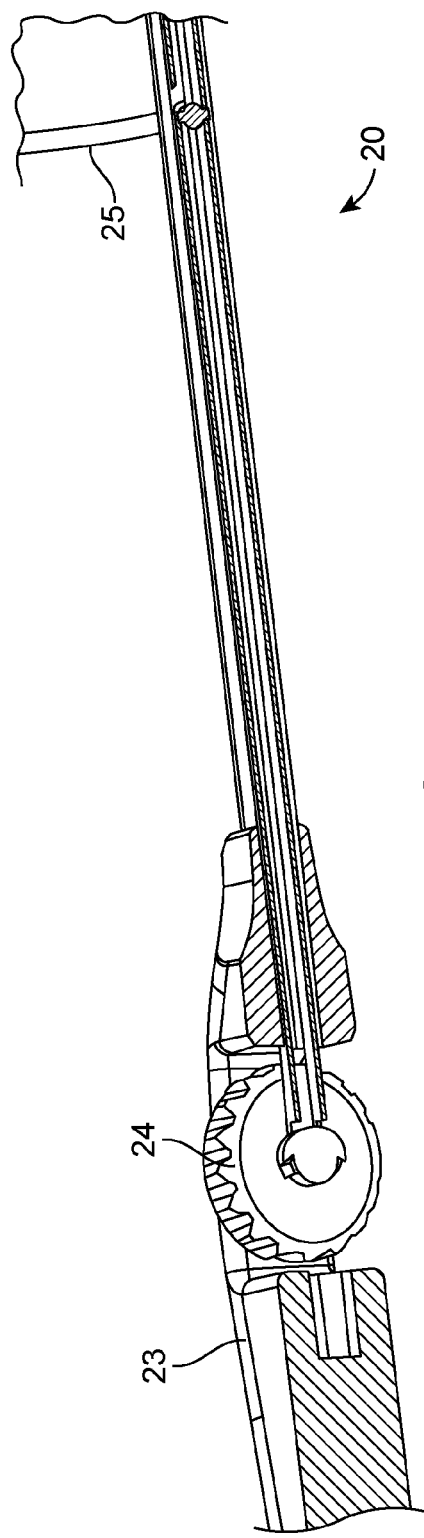

VAGINAL SPECULUM AND RELATED METHODS

CROSS-REFERENCE TO RELATED APPLICATIONS

This document claims the benefit and priority of U.S. Prov. App. Ser. No. 62/972,952 filed Feb. 11, 2020.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

REFERENCE TO AN APPENDIX SUBMITTED ON A COMPACT DISC AND INCORPORATED BY REFERENCE OF THE MATERIAL ON THE COMPACT DISC

Not applicable.

STATEMENT REGARDING PRIOR DISCLOSURES BY THE INVENTOR OR A JOINT INVENTOR

Reserved for a later date, if necessary.

BACKGROUND OF THE INVENTION

Field of Invention

Gynecological Medical Devices

Background of the Invention

The female anatomy is comprised of many unique reproductive organs. Specifically, the internal reproductive organs are the vagina, cervix, uterus, fallopian tubes, and ovaries. These organs have many functions. They are used for childbirth, sexual intercourse, procreation, and menstruation. To remain functional, these organs must remain healthy. Reproductive health has its own challenges. Women must take special steps to keep their reproductive systems healthy, as there are many medical complications which can lead to the downfall of a woman's reproductive health.

Like any other system in the human body, the health of each organ of the female reproductive system is important for the entire system to properly function. There are a wide array of common reproductive health concerns for women, some of which being endometriosis, fibroids, cancer, ovarian cysts, and sexually transmitted diseases. A woman age 21 and older should have annual physical exams, routine screenings and be evaluated if she believes she is suffering from complications related to her reproductive health. If these health concerns are not dealt with in a timely manner they may cause pain, infertility, or death.

Many steps must be taken to maintain a healthy reproductive system. An important step in maintaining a healthy reproductive system in a woman is having regular visits to a gynecologist, a type of doctor whose practice is focused on dealing with the health of the female reproductive system. If a woman believes she is having issues with her reproductive system it is important for a medical professional to actually evaluate these organs. This process is called a pelvic exam.

A pelvic exam is a physical exam of the internal and external female pelvic organs. It is used for evaluation of the female productive organs and urinary tract. It is recommended that women 21 years old and older have an annual physical examination which includes a pelvic exam. Symptoms such as pain, heavy or abnormal bleeding, discharge, or incontinence are indications that a pelvic exam is necessary. Annual screening is important because, some diseases or infections of the reproductive system may be asymptomatic. A pelvic exam may also be necessary if a woman has been sexually assaulted or to assess a woman's anatomy in preparation for a medical procedure.

The examination is performed in three steps. The first step is an external visual examination, next step is an internal visual examination using a speculum, which may include a pap smear, and the last step is an internal palpation examination. The external visual examination involves the gynecologist simply looking at the external reproductive organs with the naked eye. The internal visual exam with a speculum allows a gynecologist to view the vaginal walls and cervix. The speculum is placed inside the vaginal canal and expanded. This dilation puts the vagina and cervix in view. During this step a medical professional may also conduct a pap smear. During each step the gynecologist is looking for abnormalities such as lesions, ulcerations, discharge, or unusual growths. Internal palpation involves a medical professional palpating from inside the vagina and outside the lower abdomen. Specifically, the gynecologist is checking the condition of the uterus and ovaries.

The speculum is a necessary tool in a pelvic exam which allows for visualization of the cervix and vagina. The average length of a vaginal canal is three to four inches long. The vaginal tissue has elastic qualities which make the vagina easily collapsible, which makes the cervix and vagina very hard to view. The speculum is a tool used to retract the vaginal walls. The speculum does this by being inserted into the vagina then expanding. This retraction and expansion puts the vaginal walls and cervix in view for a medical professional.

There are many different speculum designs. They have a duck bill like shape with similar dimensions to the vagina. Speculums can have either one, two, or three blades for retraction. Speculums have different sizes for different sized women of different ages. Such speculums are made out of plastic or metal. Metal speculums are reusable and must be sterilized, while plastic speculums are disposable. Some speculums are outfitted with a light source.

The most common type of speculum is a bivalve speculum (shown in FIG. 5). The bivalve speculum has a handle, a screw, and two blades. During the exam, a medical professional starts by inserting the blades into the vagina. Then the handle is squeezed. This causes the duckbill like blades to be pulled part. Once the blades are a necessary distance apart, the screw is engaged to lock the speculum in in an open position. Once the examination is over the screw is disengaged to unlock the blades. The blades are then closed and the tool removed from the vagina.

Proper practices during the exam are an absolute necessity for patients to maintain their dignity and modesty. The gynecologist must obtain informed consent from the patient before the exam begins. Each part of the exam must be explained by the gynecologist to the patient before it is done. The patient is to be undressed only the minimum amount of time necessary to conduct the exam. These exams are conducted on sterile medical examination tables, preferably with foot supports. The patient is to be undressed from the waist down and covered with a sheet. Many exams include the presence of a chaperone, especially in the event that the medical provider is a male.

A pelvic exam may feel intrusive and uncomfortable for some women. A women's vagina is considered a private place, one which may be reserved for intimacy. It is a part of her body, and hers alone. She has the right to say what does or does not happen there. Pelvic exams may feel intrusive and invasive. They may involve an unfamiliar person entering and touching a private area of one's body with inorganic tools. These exams involve cold metal or plastic instruments. They involve invasive poking and prodding of sensitive areas. The exams are uncomfortable, unfamiliar, awkward, and perhaps violating. Inherently, these exams elicit stress and anxiety in women. Although these exams are uncomfortable, they are necessary. Thus, a need exists for a tool which can be used to retract the vagina during pelvic exams without causing women a slew of negative emotions.

SUMMARY OF THE INVENTION

In view of the foregoing, an object of this specification is to disclose a tool that comfortably dilates a woman's vagina for a pelvic exam.

It is yet another object of this specification to disclose a tool that allows for viewing of the vagina and the cervix for medical evaluation and treatments. In one embodiment, the above objectives are met by disclosing a vaginal speculum used to maintain vaginal dilation comprising: a flute; and, a expander. That apparatus could further include wherein said flute features a tunnel at a proximal end. That apparatus could further include wherein the tunnel comprises a sleeve which is a hollow cylinder made out of a film and wherein the film uses a lip and a plurality of spines to maintain its structure. In another embodiment, the above objectives are met by disclosing a tilting hoop vaginal speculum used to maintain vaginal dilation comprising: handle, a guide rod, at least one tilting hoop rotatably attached to the guide rod, and a driving mechanism disposed in the handle for tilting the hoop between a retracted configuration and a deployed configuration. That apparatus could further include wherein said driving mechanism is a rotary dial that is coupled to a foot of the hoop via two pistons that operate to push or pull the foot so that the hoop rotates between the two stated configurations.

Disclosed may also be a related method of dilating a vagina during a pelvic exam comprising: Placing a speculum in a vagina via a flute or guide rod, Expanding a tunnel via a thread or rotating a hoop disposed on the guide rod via a rotary dial until the hoop is in a deployed configuration, Contracting the tunnel via the expander or rotating the hoop via the dial until the hoop is in a retracted configuration, and, Removing the speculum via the flute or else via the guide rod.

Other objectives of the invention will become apparent to those skilled in the art once the invention has been shown and described. These objectives are not to be construed as limitations of applicant's invention, but are merely aimed to suggest some of the many benefits that may be realized by the apparatus of the present application and with its many embodiments.

BRIEF DESCRIPTION OF THE SEVERAL VIEWS OF THE DRAWINGS

Other objectives of the disclosure will become apparent to those skilled in the art once the invention has been shown and described. The manner in which these objectives and other desirable characteristics can be obtained is explained in the following description and attached figures in which:

FIG. 8 is a view of a drive mechanism of the tilting hoop speculum in a retracted state; and, FIG. 9 is a view of the drive mechanism of the tilting hoop speculum in a deployed stated.

In the figures each component of the speculum shown in the figures is labeled and indicated by the numeral as shown on the list below;

1—Flute grip
2—Expander grip
3—Catch
4—Lip
5—Spine
6—Sleeve
7—Expander
8—Flute
9—Flute neck
10—Expander neck
11—Tunnel
12—Speculum
13—Vagina
14—Cervix
15—Thread
20—tilting hoop speculum
21—guide rod
22—LED flashlight or LED light-guide
23—handle
24—drive mechanism or rotary dial
25—tilting hoop
26—driving piston
27—hoop footer It is to be noted, however, that the appended figures illustrate only typical embodiments of this invention and are therefore not to be considered limiting of its scope, for the invention may admit to other equally effective embodiments that will be appreciated by those reasonably skilled in the relevant arts. Also, figures are not necessarily made to scale but are representative.

DETAILED DESCRIPTION OF PREFFERED EMBODIMENTS

Disclosed is a preferred embodiment of the speculum. The details of the preferred embodiment are described with relevance to the figures.

Figure 1:
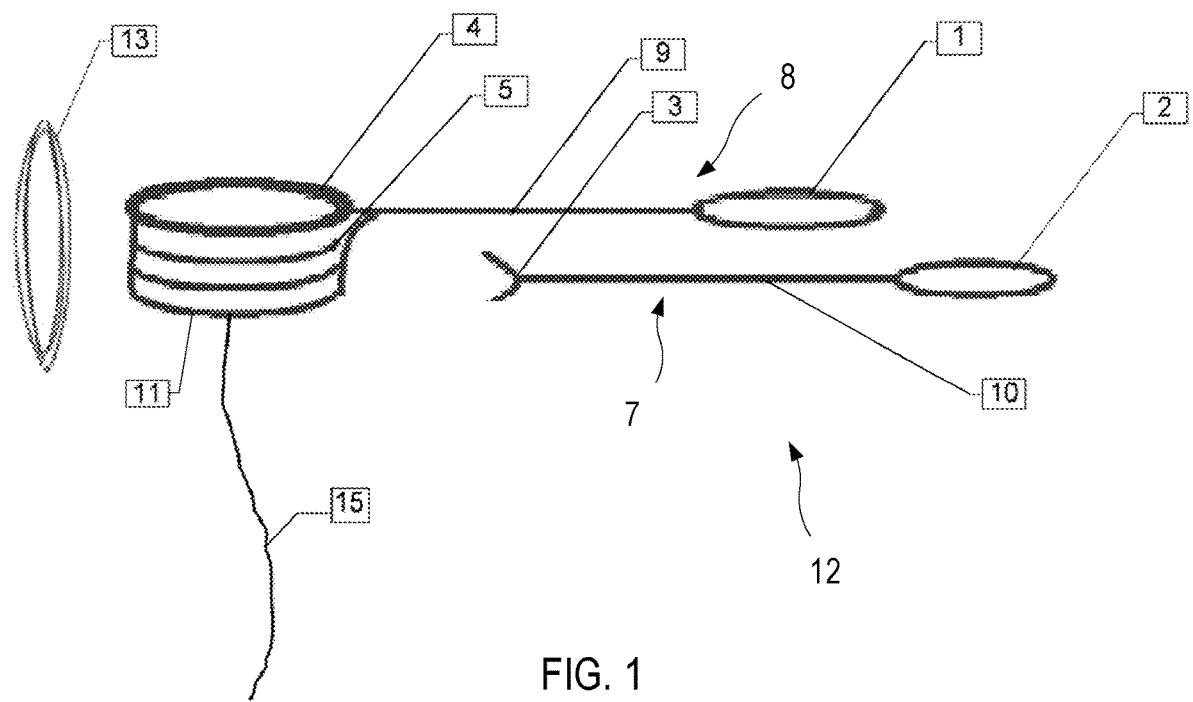
FIG. 1 is an environmental view of a preferred embodiment of the speculum in front of a vagina in a contracted position.

FIG. 1 is a perspective view of the preferred embodiment of a speculum 12. As shown, the speculum 12 is comprised of two parts, the flute 8 and the expander 7. The flute 8 may be comprised of a grip 1, a neck 9, and a tunnel 11. The grip 1 may be an single or double ellipsoid and configured to fit snugly in the palm of a hand. The neck 9 may be a thin rod which connects to the tunnel 11 on its proximal end and the grip 1 on its distal end. The tunnel 11 may be a hollow cylinder made of a clear or opaque film. The film, called a sleeve 6, may take the shape of a cylinder because it is connected to circular supports called spines 5. The proximal spine 5 may be thicker than the other spines 5 and is referred to as a lip 4. A thread comprised of a piece of string is tied to a distal spine 5. The spines 5 are, in a preferred embodiment, circular and are often in a position correspondent to that of the lip 4. The entire tunnel 11 is manipulated by moving the lip 4.

The tunnel 11 and the spines 5 of which it is comprised, as shown in FIG. 1, are an important structure of the speculum 12 because it creates the structural support necessary to dilate the vagina 13. It also puts the necessary parts of the vagina 13 into view. The flute 8 and the expander 7 are accessory tools for the tunnel 11 used for the placement, and further structural support of the tunnel 11.

The expander 7 is a tool which may be used to place and move the tunnel 11. The expander 7 may be comprised of a catch 3, a neck 10, and a grip 2. Like the flute 8, the grip of the expander 2 is preferably an ellipsoid, and the neck of the expander 10 may be a thin rod. The catch 3 is on the proximal end of the expander. The catch 3 may be configured to hook the lip 4 of the flute 8 to manipulate the tunnel 11.

Other embodiments of the speculum 12 may be constructed from different materials or composites. However, the preferred embodiment of the speculum 12 is constructed out of silicone. The speculum 12 may be made out of plastic or metal and lined with silicone.

Figure 2:
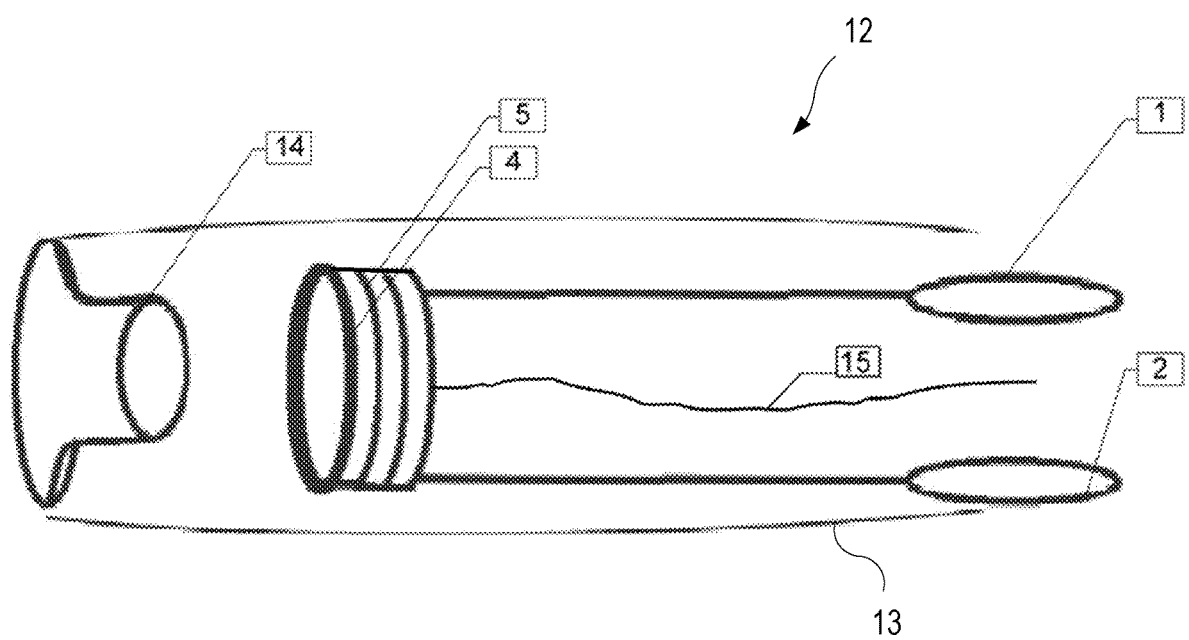
FIG. 2 is an environmental view of a preferred embodiment of the speculum inside a vagina, in an intermediate position.

In one embodiment the tunnel has three positions, each having functional significance. These positions or states are, "contracted" which is shown in FIG. 1, "intermediate" which is shown in FIG. 2, and "expanded" which shown in FIG. 3. When contracted, the lip 4 and axis of the tunnel 11 is facing upward and orthogonal to the cervix 14 and the tunnel 11 is compressed. The contracted position is the necessary position for placing the speculum 12 inside the vagina 13. The intermediate position is characterized by the lip 4 facing (coaxial) the cervix 14 and the tunnel 11 being compressed. The intermediate position is a position between the speculum 12 being placed and being used. The expanded position is characterized by the lip 4 facing (coaxial) the cervix 14 and the tunnel 11 being expanded. In the expanded position the speculum 12 is functional, dilating the vagina 13 and putting the cervix 14 and vagina 13 in view.

FIG. 1 shows the speculum 12 in its contacted state. The tunnel 11 is compressed, and all the spines 5 are stacked together. The lip 4 is orthogonal to the neck of the flute 8. This is the state the speculum 12 is in before the flute 8 is inserted into a vagina 13. The expander 7 is also separate from the flute at this point.

FIG. 2 is a perspective view of the speculum 12 inside a representation of a vagina 13. The grips 1 & 2 are used to place the tunnel 11 inside the vagina 13. The expander 7 is kept outside the vagina while still connected to the constricted tunnel 11 during insertion. The necks of the expander 7 and flute 8 are the length of a vagina 13 or longer. The speculum 12 is customizable. One size fits many, independent of vaginal depth. If a vagina 13 has a smaller diameter then a tunnel 11 with a smaller diameter may be used. A smaller tunnel 11 may be used with the same flute 8 and expander 7. This figure also shows the lip 4 as parallel to the neck 9 of the flute 8, and facing the cervix 14. The spines 5 may be thicker or stronger in various degrees for patients who are obese or experience pelvic prolapse.

Figure 3:
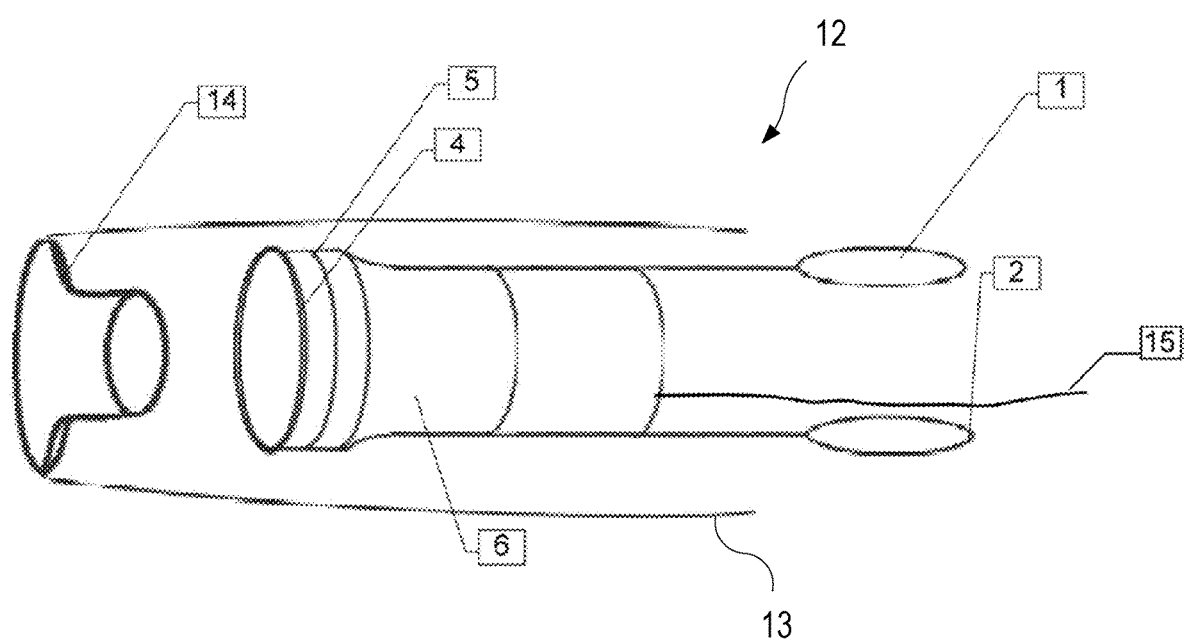
FIG. 3 is an environmental view of the speculum inside a vagina facing the cervix in an expanded position.

FIG. 3 is an environmental view of the speculum 12 inside the vagina 13 in an expanded state. Both the flute 8 and the expander 7 are inside the vagina 13 to the depth of the grips. The thread 15 has been engaged to pull the sleeve 6 down the length of the necks of both the flute 8 and the expander 7. The necks support the spines 5 of the tunnel 11. These structures are suitably designed to counteract the compressive forces of the vaginal walls. The lip 4 is facing (coaxial) the cervix 14 and the cervix 14 is in view through the tunnel 11. The sleeve 6 may preferably be made out of a clear material so that the vaginal walls are also in view.

Figure 4:
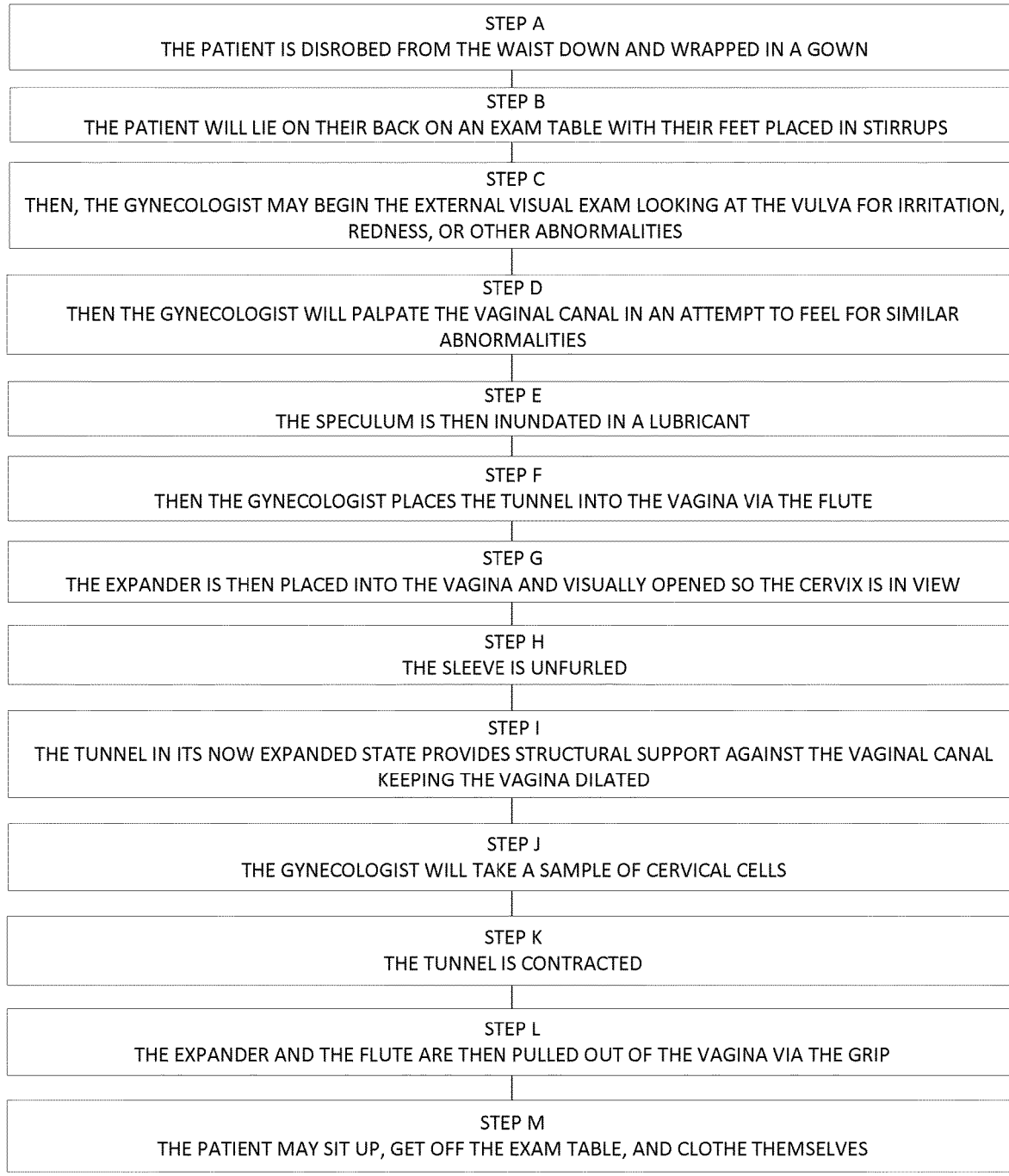
FIG. 4 is a flow chart for a pelvic exam.
Figure 5:
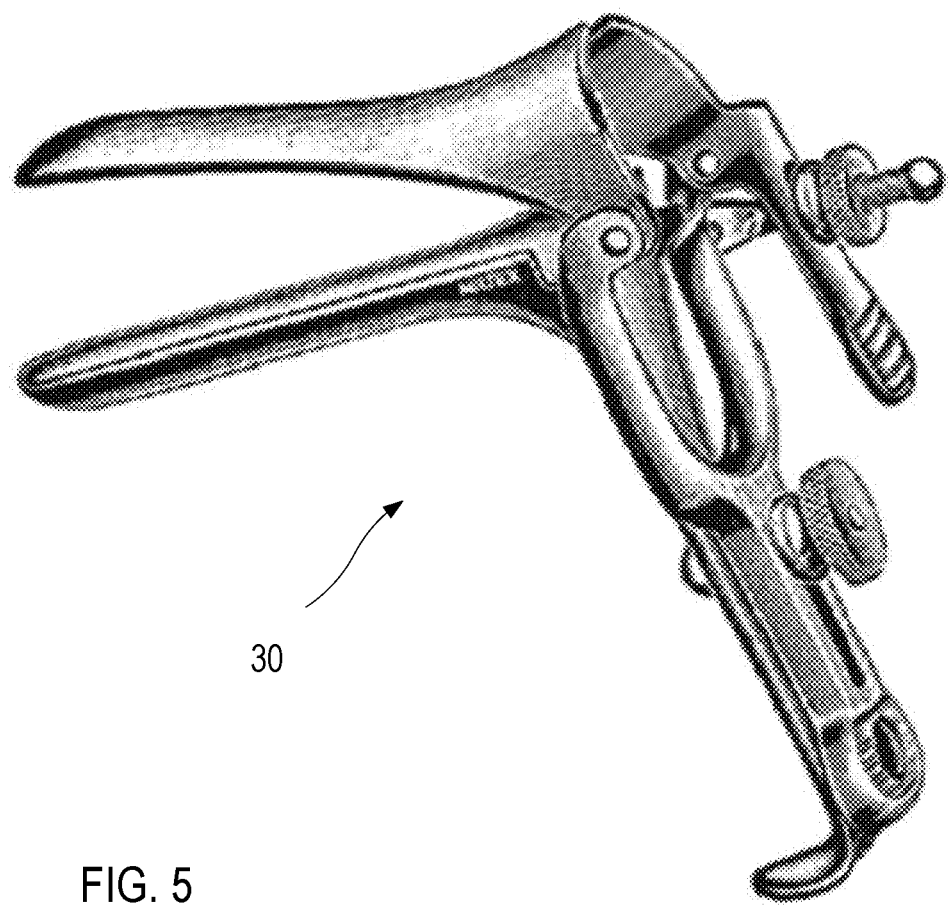
FIG. 5 is a prior art speculum.

FIG. 4 shows a flow chart of a pelvic exam which follows the same steps as the exam described below. The speculum 12 is to be used during a pelvic exam to allow a medical provider or gynecologist the ability to view the vaginal walls and cervix 14. The exam which employs the invention is in most ways similar to the exam which employs a prior art speculum. Referring to step one of FIG. 4, the exam begins by first having a patient disrobe. If the gynecologist is a male, a chaperone should be present. The patient is disrobed from the waist down and wrapped in a gown. Next, the patient will lie on their back on an exam table with their feet placed in stirrups. The patient slides to the end of the table and lets their knees open. Consent is obtained and the medical provider outlines each step of the process before the examination beings. During step 3 as per FIG. 4, the gynecologist may begin the external visual exam looking at the vulva for irritation, redness, or other abnormalities. Next, the gynecologist will use the speculum 12 of the specification to dilate the vaginal walls.

In the fifth step outlined by the flow chart in FIG. 4, the speculum 12 is inundated in a lubricant and warmed. At this point, the flute 8 and the expander 7 are held by the grips in front of the vagina 13 by the hands of the gynecologist, with the flute 8 in one hand and the expander 7 in another. The tunnel 11 is in a contracted position. The lip 4 of the tunnel and the plurality of spines 5 are facing upward. The spines 5 are stacked on top of one another. The sleeve 6 is compressed together and not taught.

Still referring to FIG. 4, the gynecologist will then instruct the patient to relax their muscles. Then the gynecologist places the tunnel 11 into the vagina 13 via the flute 8 to a necessary depth. The expander 7 is then placed into the vagina 13. The catch 3 of the expander hooks the lip 4 of the tunnel 11 and pulls the lip 4 down. This pulling causes the lip 4 to rotate. The lip 4 is rotated until it faces the cervix. The expander 7 is still latched to the lip via the catch 3. Now, the thread 15 is pulled out of the vagina 13. The sleeve 6 is unfurled and the material which comprises it is taught. The spines 5 are pulled apart. The tunnel 11 is now fully expanded. The tunnel 11 in its now expanded state provides structural support against the vaginal canal keeping the vagina 13 dilated.

The gynecologist is now able to observe the cervix 14 and the vaginal walls. Referring to FIG. 4, step 9, if a pap test is deemed necessary the gynecologist will take a sample of cervical cells. Lastly, the gynecologist will palpate the vaginal canal in an attempt to feel for similar abnormalities. During palpation the doctor will also feel the abdomen and pelvis since some organs like the uterus and ovaries cannot be seen. Then the speculum 12 is ready to be contracted. First the gynecologist uses the catch 3 of the expander 7 to hook the lip 4 of the tunnel. The gynecologist then uses the catch 3 of the expander 7 to compress the sleeve 6 and consequently, the tunnel 11. The sleeve 6 is furled and the spines 5 sit next to each other. Then the doctor uses the expander 7 to rotate the lip 4 so that the lip 4 is now orthogonal to the cervix 14. The expander 7 is then pulled out of the vagina 13 via the grip. Shortly after, the flute 8 is removed from the vagina 13 via the grip. The examination is over. Lastly, the patient may sit up, get off the exam table, and clothe themselves.

Figure 6:
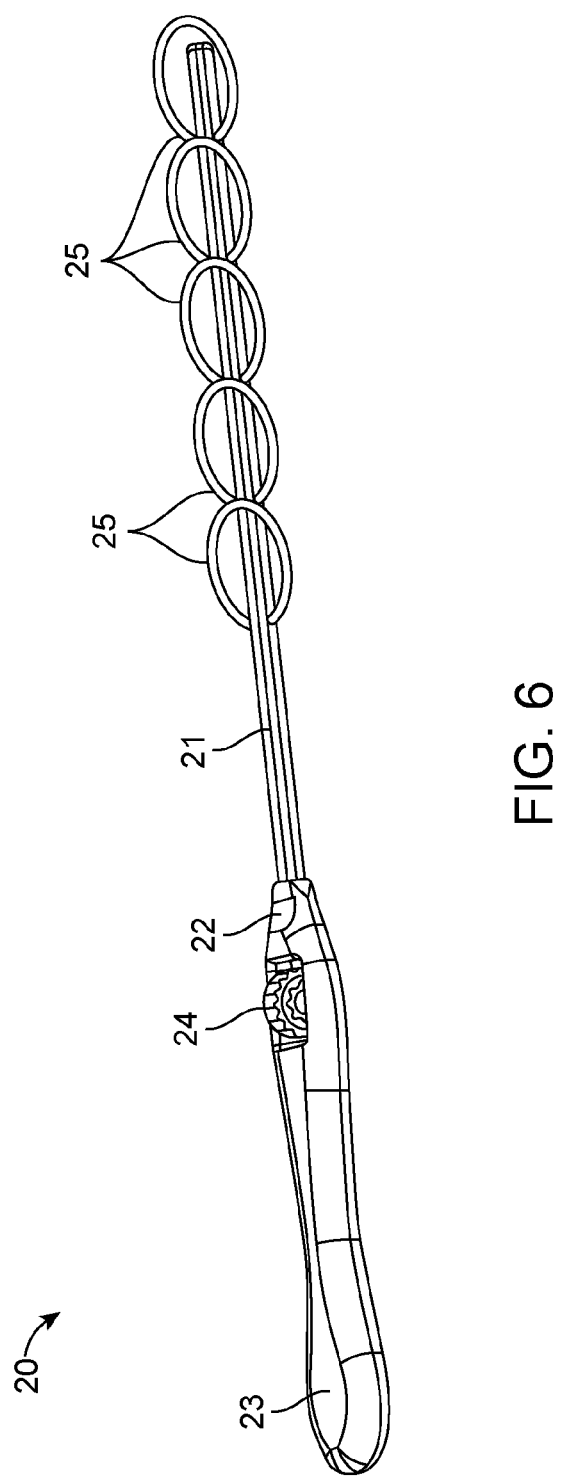
FIG. 6 is a tilting hoop speculum in a retracted state.

FIG. 6 is a perspective view of the preferred embodiment of a tilted hoop speculum 20. As shown, the speculum 20 is comprised of two main parts, the flute 8 and the guide rod 21. The may be comprised of a grip 1, a neck 9, and a tunnel 11. The grip 1 may be an single or double ellipsoid and configured to fit snugly in the palm of a hand. The neck 9 may be a thin rod which connects to the tunnel 11 on its proximal end and the grip 1 on its distal end. The tunnel 11 may be a hollow cylinder made of a clear or opaque film. The film, called a sleeve 6, may take the shape of a cylinder because it is connected to circular supports called spines 5. The proximal spine 5 may be thicker than the other spines 5 and is referred to as a lip 4. A thread comprised of a piece of string is tied to a distal spine 5. The spines 5 are, in a preferred embodiment, circular and are often in a position correspondent to that of the lip 4. The entire tunnel 11 is manipulated by moving the lip 4.

The tunnel 11 and the spines 5 of which it is comprised, as shown in FIG. 1, are an important structure of the speculum 12 because it creates the structural support necessary to dilate the vagina 13. It also puts the necessary parts of the vagina 13 into view. The flute 8 and the expander 7 are accessory tools for the tunnel 11 used for the placement, and further structural support of the tunnel 11.

The expander 7 is a tool which may be used to place and move the tunnel 11. The expander 7 may be comprised of a catch 3, a neck 10, and a grip 2. Like the flute 8, the grip of the expander 2 is preferably an ellipsoid, and the neck of the expander 10 may be a thin rod. The catch 3 is on the proximal end of the expander. The catch 3 may be configured to hook the lip 4 of the flute 8 to manipulate the tunnel 11.

Other embodiments of the speculum 12 may be constructed from different materials or composites. However, the preferred embodiment of the speculum 12 is constructed out of silicone. The speculum 12 may be made out of plastic or metal and lined with silicone.

In one embodiment the tunnel has three positions, each having functional significance. These positions or states are, "contracted" which is shown in FIG. 1, "intermediate" which is shown in FIG. 2, and "expanded" which shown in FIG. 3. When contracted, the lip 4 and axis of the tunnel 11 is facing upward and orthogonal to the cervix 14 and the tunnel 11 is compressed. The contracted position is the necessary position for placing the speculum 12 inside the vagina 13. The intermediate position is characterized by the lip 4 facing (coaxial) the cervix 14 and the tunnel 11 being compressed. The intermediate position is a position between the speculum 12 being placed and being used. The expanded position is characterized by the lip 4 facing (coaxial) the cervix 14 and the tunnel 11 being expanded. In the expanded position the speculum 12 is functional, dilating the vagina 13 and putting the cervix 14 and vagina 13 in view.

FIG. 6 shows the tilting hoop speculum 20 in its retracted state. The tunnel defined by a plurality of tiltable hoops 25 is compressed, and all the hoops 25 are tilted against the guide rod 21. The hoops 25 are parallel to the neck of the handle 23. This is the state the speculum 12 is in before the handle 23 is used to move the guide rod 21 into a vagina 13. The rotary dial is in the handle is in a first position at this point.

Figure 7:
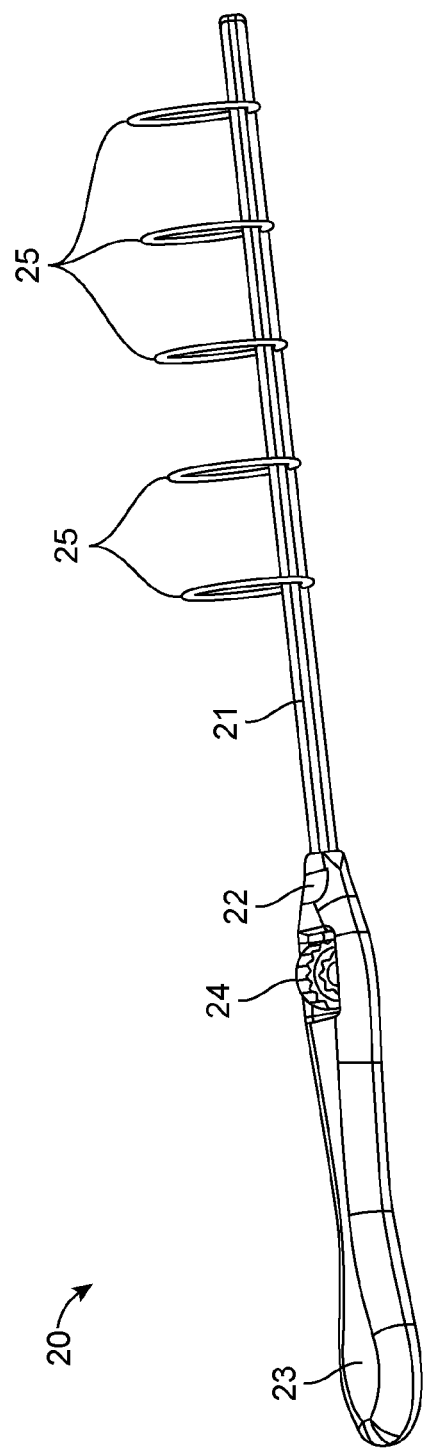
FIG. 7 is a tilting hoop speculum in a deployed state.

FIG. 7 is a perspective view of the speculum 20. The handle 23 is used to place the guide rod 21 and hoops inside a vagina (not shown). in some embodimetns there is an LED or flashlight 22 at the end of the handle 23 to act as a guide light for insertion of the guide rod 21 into a vagina (not shown). The rotary dial 24 is kept outside the vagina (not shown) but still connected to the constricted tunnel (plurality of hoops 25) during insertion via pistons 26 (not shown until FIG. 8). The guide rod 21 and handle 23 are the length of a vagina (not shown) or longer. The speculum 20 is customizable. One size fits many, independent of vaginal depth. If a vagina (not shown) has a smaller diameter then a hoop 25 with a smaller diameter may be used. A smaller hoop 25 may be used with the same handle 23 and expander 7. This figure also shows the hoops 25 as orthogonal to the guide rod 21 in a deployed position so that the hoops may be interfacing the cervix (not shown) when inserted into a vagina (not shown). The hoops 25 may be thicker or stronger in various degrees for patients who are obese or experience pelvic prolapse.

FIG. 2 may be considered an environmental view of the speculum 12 inside the vagina (not shown) in a deployed state. The guide-rod 21 and hoops 25 have been inside the vagina (not shown) to the depth of the handle 23. The rotary dial 24 has been moved to a second position to tilt the hoops up over the length of the guide rod 21. The guide-rod 21 support the hoops 25 of the tunnel. These hoop structures are suitably designed to counteract the compressive forces of the vaginal walls. The first hoop is facing (coaxial) the cervix (not shown) and the cervix (not shown) is in view through the tunnel defined by the hoops 25. A sleeve (not shown) may cover the hoops 25 to form a tunnel and preferably be made out of a clear material so that the vaginal walls are also in view.

FIGS. 8 and 9 shows a cross section of the speculum 20. As shown, the rotary dial 24 is connected at a centerpiece to two piston rods that are further connected to a foot 27 of the hoops 25. When the rotary dial is rotated, the pistons move to-and-fro to tilt the hoops between the retracted position (FIGS. 6 & 8) on one hand and the deployed position (FIGS. 7 & 9) on the other hand.

A flow of a pelvic exam follows the same steps as the exam described below. The speculum 20 is to be used during a pelvic exam to allow a medical provider or gynecologist the ability to view the vaginal walls and cervix. The exam which employs the invention is in most ways similar to the exam which employs a prior art speculum. The exam begins by first having a patient disrobe. If the gynecologist is a male, a chaperone should be present. The patient is disrobed from the waist down and wrapped in a gown. Next, the patient will lie on their back on an exam table with their feet placed in stirrups. The patient slides to the end of the table and lets their knees open. Consent is obtained and the medical provider outlines each step of the process before the examination beings. At this point, the gynecologist may begin the external visual exam looking at the vulva for irritation, redness, or other abnormalities. Next, the gynecologist will use the speculum 20 of the specification to dilate the vaginal walls.

More specifically, the speculum 20 is inundated in a lubricant and warmed. At this point, the handle 23 is held in front of the vagina (not shown) by the hands of the gynecologist, with the handle 23 in one hand. The tunnel is in a retracted position. The hoop of the tunnel and the plurality of hoops 25 are facing upward. The hoops are stacked on top of guide rod 21.

The gynecologist will then instruct the patient to relax their muscles. Then the gynecologist places the guide rod 21 into the vagina (not shown) via the handle 23 to a necessary depth. The dial 24 is then rotated so that the hoops 25 rotate.

The hopes 25 are rotated until they faces the cervix. The dial may suitably feature detents to lock the speculum in a deployed state. The tunnel of hoops 25 is now fully expanded. The tunnel of hoops 25 in its now expanded state provides structural support against the vaginal canal keeping the vagina (not shown) dilated.

The gynecologist is now able to observe the cervix and the vaginal walls. If a pap test is deemed necessary the gynecologist will take a sample of cervical cells. Lastly, the gynecologist will palpate the vaginal canal in an attempt to feel for similar abnormalities. During palpation the doctor will also feel the abdomen and pelvis since some organs like the uterus and ovaries cannot be seen. Then the speculum 20 is ready to be contracted. First the gynecologist uses the rotary dial to rotate the hoops of the tunnel to a retracted position. The sleeve 6 is retracted and the hoops 25 sit next to flat along the guide rod 21. The guide rod 21 is then pulled out of the vagina (not shown) via the handle 23. The examination is over. Lastly, the patient may sit up, get off the exam table, and clothe themselves.

Although the method and apparatus is described above in terms of various exemplary embodiments and implementations, it should be understood that the various features, aspects and functionality described in one or more of the individual embodiments are not limited in their applicability to the particular embodiment with which they are described, but instead might be applied, alone or in various combinations, to one or more of the other embodiments of the disclosed method and apparatus, whether or not such embodiments are described and whether or not such features are presented as being a part of a described embodiment. Thus the breadth and scope of the claimed invention should not be limited by any of the above-described embodiments.

Terms and phrases used in this document, and variations thereof, unless otherwise expressly stated, should be construed as open-ended as opposed to limiting. As examples of the foregoing: the term "including" should be read as meaning "including, without limitation" or the like, the term "example" is used to provide exemplary instances of the item in discussion, not an exhaustive or limiting list thereof, the terms "a" or "an" should be read as meaning "at least one," "one or more," or the like, and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that might be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases might be absent. The use of the term "assembly" does not imply that the components or functionality described or claimed as part of the module are all configured in a common package. Indeed, any or all of the various components of a module, whether control logic or other components, might be combined in a single package or separately maintained and might further be distributed across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives might be implemented without confinement to the illustrated examples. For example, block diagrams and their accompanying description should not be construed as mandating a particular architecture or configuration.

All original claims submitted with this specification are incorporated by reference in their entirety as if fully set forth herein.

I claim:

1. A method of dilating a vagina for viewing a cervix during a pelvic exam comprising:
    placing a first end of a flute of a speculum in a distal position inside the vagina with the speculum in a collapsed configuration,
    moving a plurality of circular spines into an expanded configuration with the plurality of circular spines transverse to the flute of the speculum via an expander until a grip of the expander is circumferentially spaced relative to a grip of the flute, and
    further expanding the speculum to a fully expanded configuration wherein the plurality of circular spines are spaced apart along the flute between the distal position and a proximal position near an opening of the vagina, the plurality of circular spines including at least a first circular spine spaced from a second circular spine and parallel to the second circular spine in the fully expanded configuration,
    wherein the plurality of circular spines, the flute, and the expander counteract a compressive force of a vaginal wall of the vagina to retain the speculum in the fully expanded configuration, and
    wherein the fully expanded configuration of the speculum allows viewing of the cervix while the plurality of circular spines are supported by the flute and the expander and while the compressive force of the vaginal wall of the vagina is being counteracted; and
    moving the plurality of circular spines to the collapsed configuration to remove the speculum from the vagina,
    wherein the plurality of circular spines are coaxial relative to each other in the collapsed configuration and in the expanded configuration.

2. The method of claim 1 wherein the expander attaches to a lip of the first circular spine via a catch.

3. The method of claim 2 wherein the speculum is formed of a clear material.

4. The method of claim 3 wherein the expander, the flute, and the plurality of circular spines provide structural support for the speculum.

5. The method of claim 4 wherein the plurality of circular spines are secured to the flute.

6. The method of claim 1 wherein the speculum is expanded at least partially by a thread.

* * * * *